United States Patent
Nüsser et al.

(10) Patent No.: US 7,467,929 B2
(45) Date of Patent: Dec. 23, 2008

(54) DEVICE FOR AXIALLY CONVEYING FLUIDS

(75) Inventors: Peter Nüsser, Berlin (DE); Johannes Mueller, Berlin (DE); Hans-Erhard Peters, Berlin (DE); Joerg Mueller, Berlin (DE); Werner Neumann, Berlin (DE); Kurt Graichen, Berlin (DE); Andreas Arndt, Berlin (DE)

(73) Assignee: Berlin Heart GmbH, Berlin (DE)

( * ) Notice: Subject to any disclaimer, the term of this patent is extended or adjusted under 35 U.S.C. 154(b) by 680 days.

(21) Appl. No.: 10/468,328

(22) PCT Filed: Feb. 18, 2002

(86) PCT No.: PCT/EP02/01740

§ 371 (c)(1),
(2), (4) Date: Feb. 5, 2004

(87) PCT Pub. No.: WO02/066837

PCT Pub. Date: Aug. 29, 2002

(65) Prior Publication Data

US 2004/0115038 A1    Jun. 17, 2004

(30) Foreign Application Priority Data

Feb. 16, 2001    (DE)    ................... 101 08 810

(51) Int. Cl.
*F04B 17/00*    (2006.01)
(52) U.S. Cl. .................. 417/351; 417/356; 417/420; 417/423.1; 417/423.7; 417/423.12

(58) Field of Classification Search ............... 417/351, 417/356, 420, 423.1, 423.7, 423.12
See application file for complete search history.

(56) References Cited

U.S. PATENT DOCUMENTS

| | | | |
|---|---|---|---|
| 3,139,832 A | | 7/1964 | Saunders |
| 3,608,088 A | | 9/1971 | Dorman et al. |
| 4,763,032 A | * | 8/1988 | Bramm et al. ............. 310/90.5 |
| 4,779,614 A | | 10/1988 | Moise |
| 4,898,518 A | | 2/1990 | Hubbard et al. |
| 4,944,748 A | | 7/1990 | Bramm et al. |
| 4,957,504 A | * | 9/1990 | Chardack ................... 623/3.14 |
| 5,049,134 A | | 9/1991 | Golding et al. |
| 5,078,741 A | | 1/1992 | Bramm et al. |
| 5,112,200 A | | 5/1992 | Isaacson et al. |
| 5,126,610 A | | 6/1992 | Fremerey |
| 5,147,187 A | | 9/1992 | Ito et al. |
| 5,211,546 A | * | 5/1993 | Isaacson et al. ............. 417/356 |
| 5,316,440 A | | 5/1994 | Kijima et al. |

(Continued)

FOREIGN PATENT DOCUMENTS

DE    3935502 A1    5/1991

(Continued)

*Primary Examiner*—Devon C Kramer
*Assistant Examiner*—Philip Stimpert
(74) *Attorney, Agent, or Firm*—Brinks Hofer Gilson & Lione

(57) ABSTRACT

A device for axially conveying fluids, wherein the conveyor part thereof is entirely magnetically borne and the radial bearing thereof is provided with sufficient rigidity and efficiently dampened, whereby problems encountered when passing through critical speeds and the disadvantageous effects of hydrodynamic and mechanical imbalance of the rotor are avoided. The magnetic bearing is combined with a hydrodynamic bearing.

11 Claims, 2 Drawing Sheets

U.S. PATENT DOCUMENTS

| | | | |
|---|---|---|---|
| 5,324,177 | A | 6/1994 | Golding et al. |
| 5,326,344 | A | 7/1994 | Bramm et al. |
| 5,360,317 | A | 11/1994 | Clausen et al. |
| 5,370,509 | A | 12/1994 | Golding et al. |
| 5,385,581 | A | 1/1995 | Bramm et al. |
| 5,393,207 | A | 2/1995 | Maher et al. |
| 5,399,074 | A | 3/1995 | Nosé et al. |
| 5,405,251 | A | 4/1995 | Sipin |
| 5,507,629 | A | 4/1996 | Jarvik |
| 5,575,630 | A | 11/1996 | Nakazawa et al. |
| 5,588,812 | A | 12/1996 | Taylor et al. |
| 5,601,418 | A | 2/1997 | Ohara et al. |
| 5,683,231 | A | 11/1997 | Nakazawa et al. |
| 5,686,772 | A | 11/1997 | Delamare et al. |
| 5,695,471 | A | 12/1997 | Wampler |
| 5,707,218 | A | 1/1998 | Maher et al. |
| 5,725,357 | A | 3/1998 | Nakazeki et al. |
| 5,729,065 | A | 3/1998 | Fremery et al. |
| 5,746,575 | A | 5/1998 | Westphal et al. |
| 5,803,720 | A | 9/1998 | Ohara et al. |
| 5,863,179 | A | 1/1999 | Westphal et al. |
| 5,947,703 | A | 9/1999 | Nojiri et al. |
| 5,951,263 | A | 9/1999 | Taylor et al. |
| 6,053,705 | A * | 4/2000 | Schob et al. .................. 417/53 |
| 6,080,133 | A | 6/2000 | Wampler |
| 6,100,618 | A | 8/2000 | Schoeb et al. |
| 6,135,729 | A * | 10/2000 | Aber .......................... 417/420 |
| 6,234,772 | B1 | 5/2001 | Wampler et al. |
| 6,234,998 | B1 | 5/2001 | Wampler |
| 6,368,075 | B1 * | 4/2002 | Fremerey ..................... 417/365 |
| 6,368,083 | B1 | 4/2002 | Wampler |
| 6,688,861 | B2 | 2/2004 | Wampler |
| 2002/0094281 | A1 | 7/2002 | Khanwilkar et al. |
| 2002/0102169 | A1 | 8/2002 | Wampler |
| 2004/0234397 | A1 | 11/2004 | Wampler |

FOREIGN PATENT DOCUMENTS

| | | |
|---|---|---|
| EP | 583781 A1 | 2/1994 |
| JP | 03286775 A | 12/1991 |
| JP | 05-071492 * | 3/1993 |
| JP | 06218043 A | 8/1994 |
| WO | WO 9307388 A1 | 4/1993 |
| WO | WO 9409274 A1 | 4/1994 |
| WO | WO 9413955 A1 | 6/1994 |
| WO | WO 9500185 A1 | 1/1995 |
| WO | WO 97/49440 A2 | 12/1997 |
| WO | WO 9811650 | 3/1998 |
| WO | WO 9811650 A1 * | 3/1998 |
| WO | WO 00/64030 A1 | 10/2000 |
| WO | WO 00/64031 * | 10/2000 |
| WO | WO 00/64508 A1 | 11/2000 |

* cited by examiner ohne 1 dargestellt ohne 1 dargestellt ohne 1 dargestellt ohne 1 dargestellt

DEVICE FOR AXIALLY CONVEYING FLUIDS

BACKGROUND

The invention relates to a device for axially conveying fluids.

In particular, less stable multiple-phase fluids which can undergo irreversible changes caused by an energy input, such as in the case of emulsions and dispersions, can run into unstable ranges in a disadvantageous manner when being conveyed in corresponding devices such as pumps.

Blood is a particularly sensitive fluid system. This opaque red body fluid of the vertebrates circulates in a self-enclosed vessel system where rhythmic contractions of the heart press the blood into various areas of the organism. In this case, the blood transports the respiratory gases oxygen and carbon dioxide as well as nutrients, metabolic products and endogenous active ingredients. The blood vessel system including the heart is hermetically isolated from the environment so that, in a healthy organism, the blood does not undergo any changes, except for the material exchange with the body cells, when it is pumped through the body by way of the heart.

It is known that, when blood comes into contact with non-endogenous materials or as a result of the effect of energy from an external source, it has a tendency to hemolysis and clot formation. Clot formation can be fatal for the organism because it can lead to blockage in the extensive branching profile of the vessel system. Hemolysis describes the condition where the red blood cells are destroyed within the body beyond the physiological dimension.

The causes for hemolysis can be of a mechanical or metabolic nature. Increased hemolysis causes multiple organ damage and can lead to a person's death.

On the other hand it is evident that it is possible in principle, under certain prerequisites with reference to constructive aspects, to support the pumping capacity of the heart or even to replace the natural heart with a synthetic one. However, a continuous operation of implanted heart supporting systems or synthetic hearts is presently only possible with certain limitations because the interactive effects of these artificial products with the blood and the entire organism still always lead to disadvantageous changes of the blood and the organism.

In the state of the art, axial blood pumps are known which mainly consist of a cylindrical tube in which a conveying part, which is executed as a rotor of an externally located motor stator, rotates. The rotor which is provided with a so-called blading, conveys the fluid in an axial direction after it has been made to rotate. The bearing of these so-called axial pumps represents a major problem. A purely mechanically bearing is disadvantageous with regard to blood damage and also the relatively high friction levels. And the magnet bearing variants as described up to the present have not, in particular, led to any satisfactory solution for the bearing conditions in axial pumps.

In the WO 00/64030 a device for the protective conveying of single- and multiple phase fluids is described whose conveying part is exclusively magnetically bearing-located. For this purpose, permanent magnetic bearing elements for the magnet bearing-location as well as permanent magnetic elements for the functionality as a motor rotor of an electromotor are preferentially integrated in the conveying part. The use of a magnet bearing for the conveying facility as described here makes it possible to waive bearing elements normally arranged in the flow current of the fluid to be conveyed which lead to dead water zones and vorticities of the fluid to be conveyed and, subsequently, have a negative influence on the current flow.

The magnetic bearing described here accommodates both the axial as well as the radial forces. The axial location of the conveying part is actively stabilised whereas the radial bearing of the conveying part is effected exclusively passive by means of the existing permanent magnets. However, the conveying facility as described has several disadvantages.

The passive magnetic radial bearing is characterised by relatively low rigidity and dampening where, during the pumping action, problems occur when passing through critical speeds of the rotor and/or the bearing. Possibly existing hydrodynamic and mechanical imbalance of the rotor has serious effects on the function of the pump, particularly when used as a blood-conveying facility.

SUMMARY

The invention is based on the task assignment of presenting a device for the axial conveying of fluids whose conveying part is completely magnetically borne and whose radial bearing has sufficient rigidity and effective dampening so that problems encountered when passing through critical speeds and the disadvantageous effects of hydrodynamic and mechanical imbalance of the rotor are avoided.

The solution for the task assignment is effected with a device for axially conveying fluids consisting of a tube-shaped hollow body which conducts the fluid in an essentially axial manner, in which a magnetically borne conveying part is arranged in axial alignment with a motor stator located outside of the hollow body capable of rotating said conveying part, where the one conveying part having a magnetic bearing has rotor blading, wherein the magnetic bearing is combined with a hydrodynamic bearing.

Further advantageous embodiments are stated in the Sub-claims.

The bearing of the conveying part has an actively stabilising magnetic axial bearing, a passive magnetic radial bearing and a hydrodynamic radial bearing. The hydrodynamic radial bearing is executed in a further embodiment of the invention as a hollow-cylindrical, rotation-symmetrical back-up ring which is joined to the conveying part.

On the conveying part, at least one back-up ring is arranged, where the back-up rings are arranged at the beginning of the motor rotor and/or at the end of the motor rotor or between these said positions.

In a further embodiment of the invention, the axial dimension of the back-up ring corresponds, at the maximum, to the axial length of the conveying part, and the axial dimension of the running surface of the back-up ring is smaller than one internal surface of the back-up ring.

The back-up ring has the same radial dimension as the rotor blading and is joined to it.

Furthermore as an embodiment, the back-up ring has such a radial dimension (thickness) that it can be provided with a radial profile which services the purpose of conditioning the inflow into the rotor blading of the conveying part.

In a further embodiment, a back-up ring is provided with such an axial reach that the blading over its entire length is restricted radially from the back-up ring. The running surface of the back-up ring which points against internal side of the tube-shaped hollow body, has in an advantageous manner a surface coating with emergency run characteristics and this coating is, moreover, bio-compatible.

The internal surface of the back-up ring has, in one execution, a profile which can favourably influence the current flow properties.

The execution of the running surface of the back-up ring as one running line leads to particularly favourable friction values.

The major rigidity and dampening of the radial bearing of the conveying part is achieved in such a way that, in addition to a magnetic bearing of the conveying part, a hydrodynamic bearing is envisaged. The hydrodynamic bearing is achieved by at least one hollow-cylindrical, rotation-symmetrical back-up ring which is solidly joined to the conveying part. With a suitable execution of the back-up ring, the rotor receives major tilting rigidity. Advantageously, this effect is obtained by a particularly large axial reach of the back-up ring or by the arrangement of at least two back-up rings at one rotor.

With a large axial reach of the back-up ring and/or extensive or complete encapsulation of the blading by means of such a back-up ring, damaging effects of the radial gap occurring at the blade ends are advantageously avoided.

The invention is explained in greater detail based on a drawing:

DESCRIPTION OF PREFERRED EMBODIMENT

Figure 1:
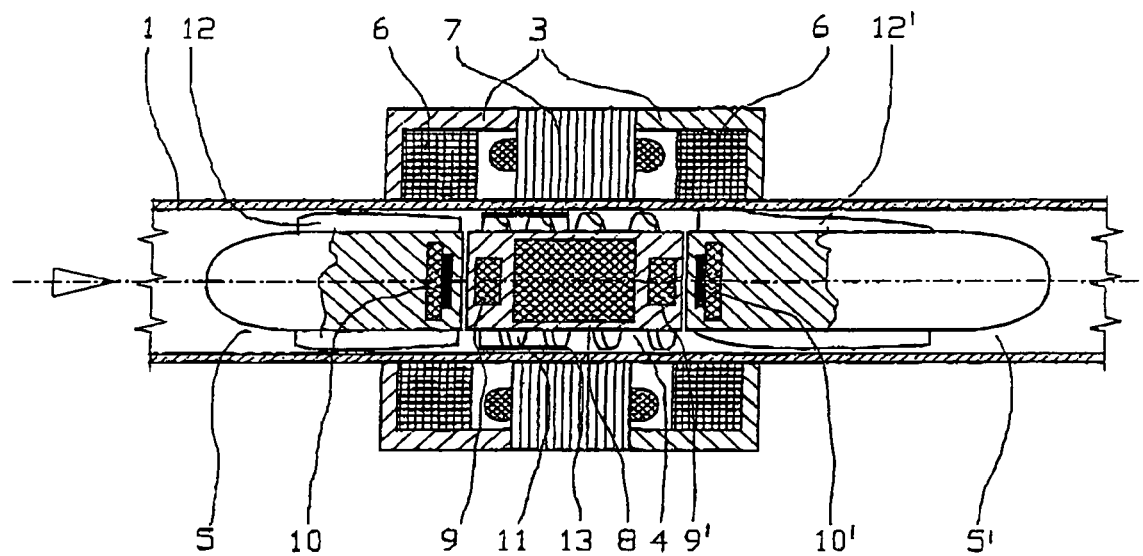
FIG. 1: a schematic illustration of an axial section of an axial blood pump with back-up ring.

In an exemplary manner, FIG. 1 shows in an axial sectional illustration the construction of a category-related axial pump with the bearing, according to the invention, of a conveying part 4. In its main parts, the axial pump consists of a tube-shaped hollow body 1 and a pump casing 3 that includes a motor stator 7 and axial stabilisers 6. The pump casing 3 lies immediately and rotation-symmetrical on the tube-shaped hollow body 1. In the interior of the tube-shaped hollow body 1, a fluid inlet guide facility 5 and a fluid outlet guide facility 5' are envisaged, between which the conveying part 4, which is rotated by the motor stator 7, is arranged.

The conveying part 4 has a magnetic bearing where permanent magnetic bearing elements 9 and 9' are arranged in the motor rotor 8 and permanent magnetic bearing elements 10 and 10' are arranged in the fluid inlet- and fluid outlet guide facilities 5 and 5'. On the motor rotor 8 of the conveying part 4, a rotor blading 11 is envisaged which is combined with a back-up ring. The magnetically bearing-located conveying part 4 is rotated by way of the motor stator 7 where, by means of the oppositely located permanent magnetic bearing elements 9, 9' and 10, 10' in combination with the axial stabilisers 6, the conveying part is kept in a floating state and the back-up ring provides for an additional hydrodynamic bearing-location of the rotating conveying part 4.

Figure 2:
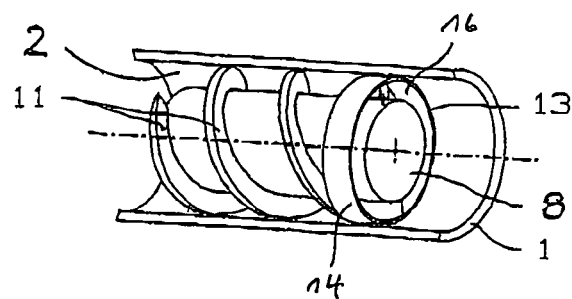
FIG. 2: a schematic illustration of an arrangement of a back-up ring on the rotor.

FIG. 2 shows in a schematic illustration the motor rotor 8 with the rotor blading 11 in a cut-open tube-shaped hollow body 1. In accordance with the invention, the back-up ring here is arranged in the end zone of the motor stator 8. The fluid to be conveyed is moved between an internal surface 16 of the back-up ring 13 and the motor rotor 8. A running surface 14 of the back-up ring 13 is moved with a minimum clearance to an internal wall 2 of the tube-shaped hollow body 1.

Figure 3:
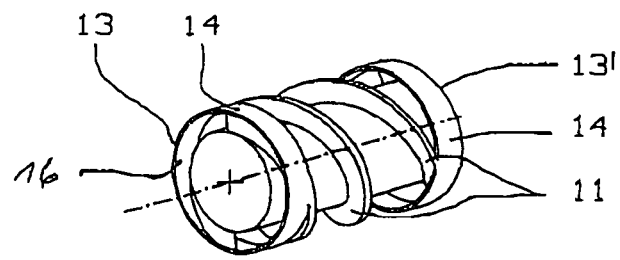
FIG. 3: a schematic illustration of an arrangement of two back-up rings on the rotor.

FIG. 3 shows in schematic illustration an arrangement of two back-up rings 13 and 13' at the ends of a motor rotor 8. The illustration of the tube-shaped hollow body 1 has been left out here.

Figure 4:
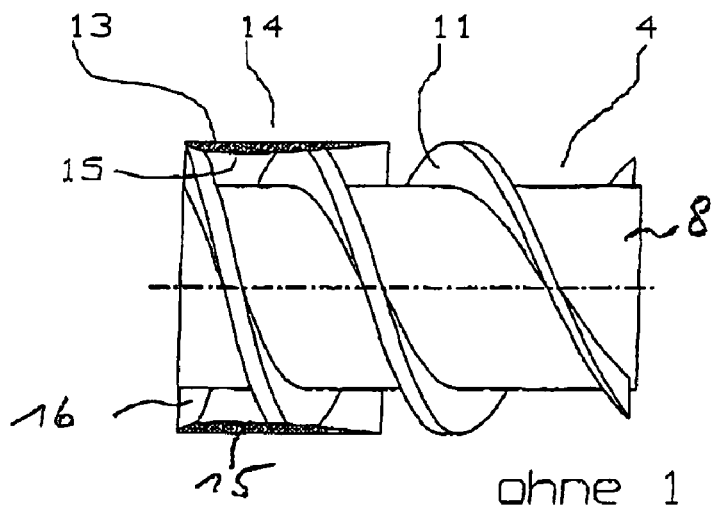
FIG. 4: a schematic illustration of an arrangement of a back-up ring with profiled internal surface.

FIG. 4 shows a further embodiment, according to the invention, of the back-up ring 13. The internal surface 16 of the back-up ring 13 shows a profile 15. As can be seen in the sectional illustration of the back-up ring 13, the profile 15 is executed here in a bearing-surface similar form. In this case also, the illustration of the tube-shaped hollow body has been waived.

Figure 5:
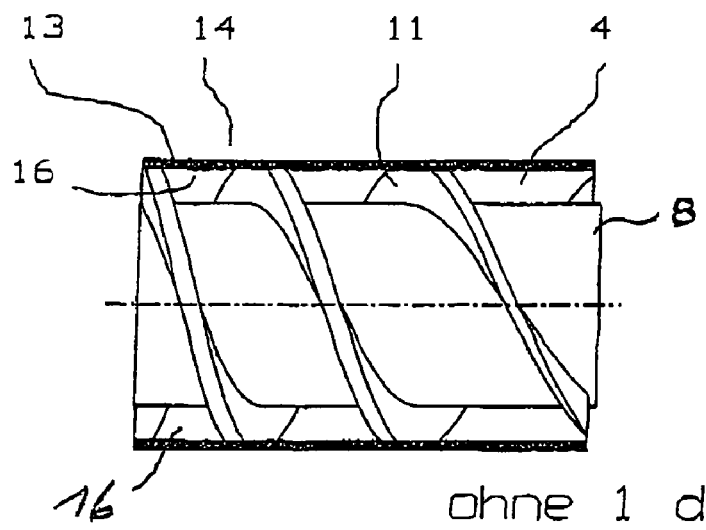
FIG. 5: a schematic illustration of a back-up ring reaching over the entire rotor.

In a further embodiment of the invention, as shown in FIG. 5, a back-up ring 13 is arranged without an illustration of the tube-shaped hollow body 1, and this back-up ring covers the entire axial length of the motor rotor 8 with its blading 11. The conveying of the fluid is also effected here between the internal surface 16 of the back-up ring 13 and the motor rotor 8.

Figure 6:
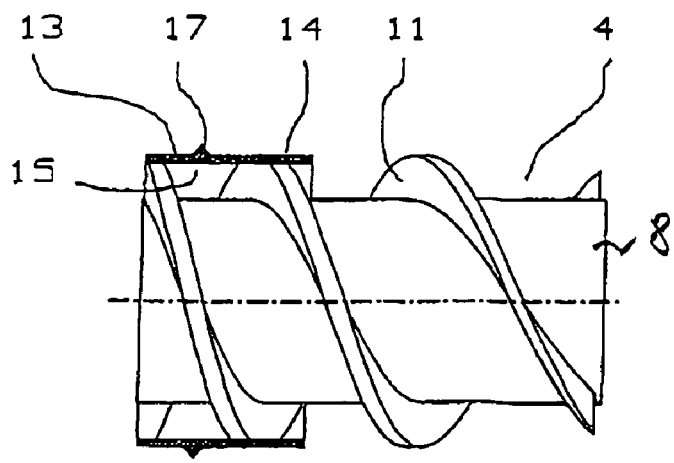
FIG. 6: a schematic illustration of a back-up ring on the rotor with a running line on the running surface.

In a further embodiment of the invention, a back-up ring is shown in FIG. 6 whose running surface 14 has a raised running line 17 which facilitates a minimum clearance combined with a minimum friction opposite the internal wall 2 of the tube-shaped hollow body 1.

REFERENCED PARTS LIST

1 Tube-shaped hollow body
2 Internal wall
3 Pump casing
4 conveying part
5 Fluid inlet guide facility
5' Fluid outlet guide facility
6 Axial stabiliser
7 Motor stator
8 Motor rotor
9 Permanent magnetic bearing element
9' Permanent magnetic bearing element
10 Permanent magnetic bearing element
10' Permanent magnetic bearing element
11 Rotor blading
12 Fluid guide blading
12' Fluid guide blading
13 Back-up ring
13' Back-up ring
14 Running surface
15 Profile
16 Internal surface
17 Running line

The invention claimed is:

1. A device for axially conveying fluids, comprising: a tube-shaped hollow body having a constant internal diameter for conducting fluid in an essentially axial manner, a motor stator located outside of the hollow body, a conveying part responsive to the motor stator and arranged within the hollow body in axial alignment with the hollow body, the conveying part including a central motor rotor having a continuous outer surface extending between a first end and a second end, blading fixed to the continuous outer surface for conveying fluid within the hollow body upon rotation of the conveying part by the motor stator, at least one hollow ring fixed to a radial outer portion of the blading defining a hydrodynamic radial bearing, the hollow ring defining the hydrodynamic radial bearing having an inner surface that is radially inwardly bowed toward the central rotor continuous outer surface for conditioning the fluid inflow into the rotor blading of the conveying part, an actively stabilizing magnetic axial bearing, and a passive magnetic radial bearing located within the hollow body, the bearings maintaining the conveying part within the tube-shaped hollow body in proximity to the motor stator.

2. A device according to claim 1, further comprising a fluid inlet guide facility and a fluid outlet guide facility, both of the guide facilities being situated in axial alignment within the tube-shaped hollow body and spaced from opposite ends of the conveying part, a permanent magnet being situated in each of the guide facilities adjacent the conveying part.

3. A device according to claim 1 or claim 2, wherein the blading fixed to the continuous outer surface of the central rotor extends from the first end to the second end, and another permanent magnet is situated in each of the ends of the rotor confronting the guide facilities.

4. A device according to claim 1 or claim 2, wherein the at least one ring defining the hydrodynamic radial bearing comprises at least one hollow, rotationally-symmetrical ring joined to the conveying part.

5. A device according to claim 4, wherein the at least one hollow, rotationally-symmetrical ring defining the hydrodynamic radial bearing is joined circumferentially to the blading at the first end.

6. A device according to claim 5, wherein a second hollow, rotationally-symmetrical ring is joined circumferentially to the blading at the second end.

7. A device according to claim 5, wherein the hollow, rotationally-symmetrical ring defining the hydrodynamic radial bearing extends entirely between the first end and the second end.

8. A device according to claim 4, wherein the at least one hollow, rotationally-symmetrical ring defining the hydrodynamic radial bearing has a cylindrical outer surface spaced from an inner surface of the tube-shaped hollow body.

9. A device according to claim 1, wherein the cylindrical outer surface of the hydrodynamic radial bearing includes an outwardly extending circumferential running line facilitating a minimum clearance and a minimum friction with the internal surface of the tube-shaped hollow body.

10. A device according to claim 1 or claim 2 wherein the at least one hollow ring is non-magnetic.

11. A device for axially conveying fluids, comprising: a tube-shaped hollow body having a constant internal diameter for conducting fluid in an essentially axial manner from a first end to a second end, a motor stator located outside of the hollow body, a conveying part responsive to the motor stator and arranged within the hollow body in axial alignment with the hollow body, the conveying part including a central rotor having a continuous outer surface extending between the first end and the second end, blading fixed to the continuous outer surface for conveying fluid within the hollow body upon rotation of the conveying part by the motor stator, a hollow non-magnetic ring fixed to a radial outer portion of the blading at the first end defining a hydrodynamic radial bearing, the hollow non-magnetic ring defining the hydrodynamic radial bearing having an inner surface that is radially inwardly bowed toward the central rotor continuous outer surface for conditioning the fluid inflow into the rotor blading of the conveying part, an actively stabilizing magnetic axial bearing, and a passive magnetic radial bearing, the bearings maintaining the conveying part within the tube-shaped hollow body in proximity to the motor stator.

* * * * *